United States Patent [19]
Mattchen

[11] Patent Number: 6,093,190
[45] Date of Patent: Jul. 25, 2000

[54] BONE FIXATION APPARATUS AND METHOD

[75] Inventor: Terry M. Mattchen, Santa Barbara, Calif.

[73] Assignee: Poly-4 Medical Inc., Santa Barbara, Calif.

[21] Appl. No.: 09/132,965

[22] Filed: Aug. 12, 1998

[51] Int. Cl.[7] .................................................. A61B 17/56
[52] U.S. Cl. .............................................. 606/74; 606/78
[58] Field of Search ................................. 606/72–76, 78, 606/54, 57–59, 60–64, 86, 103, 213, 215, 216, 232–233

[56] References Cited

U.S. PATENT DOCUMENTS

| | | | |
|---|---|---|---|
| 3,741,205 | 6/1973 | Markolf et al. | 128/92 |
| 3,877,424 | 4/1975 | Murray | 128/92 |
| 4,655,203 | 4/1987 | Tormala et al. | 128/92 |
| 4,688,561 | 8/1987 | Reese | 128/92 |
| 4,778,468 | 10/1988 | Hunt et al. | 623/16 |
| 4,813,869 | 3/1989 | Gatewood | 128/89 |
| 4,852,559 | 8/1989 | Chernoff | 128/92 |
| 4,858,603 | 8/1989 | Clemow et al. | 128/92 |
| 5,092,866 | 3/1992 | Breard et al. | 606/61 |
| 5,108,397 | 4/1992 | White | 606/60 |
| 5,201,733 | 4/1993 | Etheredge, III | 606/53 |
| 5,324,291 | 6/1994 | Ries et al. | 606/71 |
| 5,474,554 | 12/1995 | Ku | 606/72 |
| 5,634,926 | 6/1997 | Jobe | 606/69 |
| 5,665,088 | 9/1997 | Gil et al. | 606/69 |
| 5,676,667 | 10/1997 | Hausman | 606/69 |
| 5,697,934 | 12/1997 | Huebner | 606/103 |

OTHER PUBLICATIONS

Hans K. Uhthoff and Francois L. Dubuc; Bone Structure Changes in the Dog Under Rigid Internal Fixation; Clinical Orthopaedics and Related Research; 1971; vol. 81, pp. 165–170.

Hans K. Uhthoff and Maureen Finnegan; The Effects of Metal Plates on Post–Traumatic Remodelling and Bone Mass; The Journal of Bone and Joint Surgery; vol. 65 B No. 1 Jan. 1983; pp. 66–71.

R. Bruce Heppenstall; Fracture Treatment and Healing; Fracture Treatment & Healing; 1980; pp. 41–45 and 140–144.

Carl T. Brighton; Biophysics of Fracture Healing; Fracture Treatment & Healing; 1980; pp. 65–70.

Martin; Theoretical Analysis of the Piezoelectric Effect in Bone; Biomechanics vol. 12, pp. 55–63; Jul. 5, 1978.

Humberto F. Boggiano; Pseudarthrosis of Tibia Treated with the Elastic Compression Technique; The Journal of Orthopaedic Surgical Techniques; vol. 6. No. 1, 1991, pp. 9–37.

Annon Foux, Alan J. Yeadon, and Hans K. Uhthoff; Improved Fracture Healing with Less Rigid Plates; Clinical Orthopaedics and Related Research; No. 339, pp. 232–245.

*Primary Examiner*—Michael Buiz
*Assistant Examiner*—Jonathan D. Goldberg
*Attorney, Agent, or Firm*—Oppenheimer Wolff & Donnelly LLP

[57] ABSTRACT

A bone fixation apparatus and method for repairing fractured bones is provided. A first pin is located on the bone adjacent the fracture and a flexible line is led to a second pin located on the other side of the fracture. A third pin is provided spaced from the first pin on the same side of the fracture and the flexible line is extended from the second pin to the third pin. A fourth pin is provided spaced from the second pin on the same side of the fracture and the flexible line is extended from the third pin to the fourth pin. Finally, the flexible line is extended from the fourth pin back to the first pin. The flexible line may be doubled up. A similar arrangement of pins and flexible line is made diametrically on the opposite side of the bone.

11 Claims, 2 Drawing Sheets

BONE FIXATION APPARATUS AND METHOD

BACKGROUND OF THE INVENTION

1. Field of the Invention

The invention relates to bone fixation; and, more particularly, to apparatus and method for repairing bone fractures.

2. Related Art

Various surgical plates have been employed in the treatment of traumas to facial or cranial bone structure, plastic surgery, reconstructive facial surgery, and the like to hold the bone sections or fragments in place during the healing process. The surgical plates are positioned against the surface of the bone sections which must be held together and fixed to the bone by mechanical fasteners such as bone screws, wire sutures, or other fasteners which secure the plate to the bone surface. The fasteners are securely pressed or embedded in the bone to prevent the surgical plates from being pulled away from the surface of the bone sections. U.S. Pat. Nos. 4,966,599 and 5,290,281 disclose examples of bone stabilization plates which are secured to the bone structure, for example, facial or cranial bones, by bone screws. U.S. Pat. No. 4,655,203 discloses a surgical device for immobilization of bone fracture which include a stiff plate and stiff fixing elements which may be pressed into notches formed in the bone.

Thus, present methods of bone fixation are:

Bone plates

Wire tension bands

Screws

Intramedullary rods

Cerclages (tie wraps; nylon, metal, or wire)

External fixation (pins and frame)

All of these prior art methods are inherently distinct and each seems to be the method of choice for certain fracture cases. There is also considerable agreement on the indications and contraindications as to when each is used.

The bone plate attains compression of the fragments through a wedge geometry of the slot in which the screw hole rides. As the screw is tightened, the wedge geometry of the slot forces the plate to the right while pulling the bone fragments into position and compression. The amount of compression depends on many variables; access to the surgical site, the fit of the bone to the plate and how accurately the screws are placed in the holes. The distribution of the compressive forces are located around the plate. Also the plate is most likely to have six to eight screws.

This surgical procedure requires some skill; the plate must be contoured to the bone and the holes must be drilled accurately to get proper reduction and compression.

An undesirable consequence of the bone plate is the fact that, after a short time, it changes the stress flow in the bone by becoming a stress shield which weakens the bone. As a result it is usually removed. The bone plate may also produce a pressure necrosis on the bone and periosteum. They promote the formation of adhesions between the gliding planes and can produce a bursa-like irritation. Consequently, these can interfere with rehabilitation, and they should be removed when they are no longer of benefit. See Uhthoff, H. K., and Dubc, F. L. (1971): "*Bone structure changes in the dog under rigid internal fixation*" Clinical Orthrop. Rel. Res., 81:165–170 and Uhthoff, H. K., and Finnegan, M. (1983): "*The effects of metal plates on post traumatic remodeling and bone mass*" J. Bone Joint Surg., 1983 65-B:66–71.

Wire used to hold bone fragments together is usually passed through drilled holes, looped and tied. It is not practical at all for the metal wire to put compression into the bone. For it to do so the wire must be stretched like an elastic. But this is an impractical application for a wire because its elongation is such a tiny percentage of the length. Also, because of the relative strengths of the wire to bone, the bone will always fail in bearing before the metal wire will stretch. To use wire as a tension band means that the wire can hold the bone fragments in approximate location and can take out tension loads but it cannot apply an active form of compression into the fragments.

Screws (lag screw) used by themselves work only in special case where the break is overlapping sufficiently for the screw to go through both walls of the bone. Screws add compression in that direction only (traverse) and not axially where it can be the most beneficial. Screws can be used in comminuted fractures but only under specific conditions.

Cerclage bands that wrap around the bone again work only in ideal cases where the break provides sufficient overlap. Like screws, they work only in circumferential compression (no axial compression).

Intramedullary rods are used primarily in the long bones of the body, such as the femur. They are inserted into the femur above and just inside the greater trochanter and down the intramedullary canal. At present, there is an increasing agreement that a procedure known as Kuntscher's intramedullary nail, supplemented with interlocking design, is the treatment of choice for essentially all closed fractures of the femur located between the lesser trochanter and femoral condyles, regardless of the fracture pattern or degree of comminution.

External fixation consists of large diameter wire rods that go through the limb and bone completely to an external frame. Usually there are 4, 6, or 8 wires through the limb to hold the fractured bones in position. External fixation is used primarily for serious fractures, most likely comminuted, where access to the fracture site is compromised, and/or orientation of fragments difficult. They are most commonly used with severe open fractures and considerable soft tissue damage. The patient must deal with a very inconvenient and bulky device for a long time. There is also a risk for infection over the length of time it is installed.

There is thus a need for a process for holding bone fragments in tight approximation while allowing a small amount of load variability which encourages bone regeneration.

SUMMARY OF THE INVENTION

It is an object of this invention to provide an apparatus and method for holding bone fragments in tight approximation while allowing a small amount of load variability which encourages bone regeneration.

It is a further object of this invention to provide a bone fixation process which promotes early bone healing and maintains the patient's joints and allows the patient to be mobile during the repair process thus reducing therapy time.

These and other objects are preferably accomplished by providing a bone fixation apparatus and method wherein a first pin is located on the bone adjacent the fracture and a flexible line is led to a second pin located on the other side of the fracture. A third pin is provided spaced from the first pin on the same side of the fracture and the flexible line is extended from the second pin to the third pin. A fourth pin is provided spaced from the second pin on the same side of the fracture and the flexible line is extended from the third pin to the fourth pin and secured. Finally, the flexible line is extended from the fourth pin back to the first pin. The flexible line may be doubled up. A similar arrangement of pins and flexible line is made on the opposite side of the bone. Any suitable anchoring means for the flexible line, such as holes, screws, etc. can be used.

DESCRIPTION OF THE PREFERRED EMBODIMENT

Figure 1:
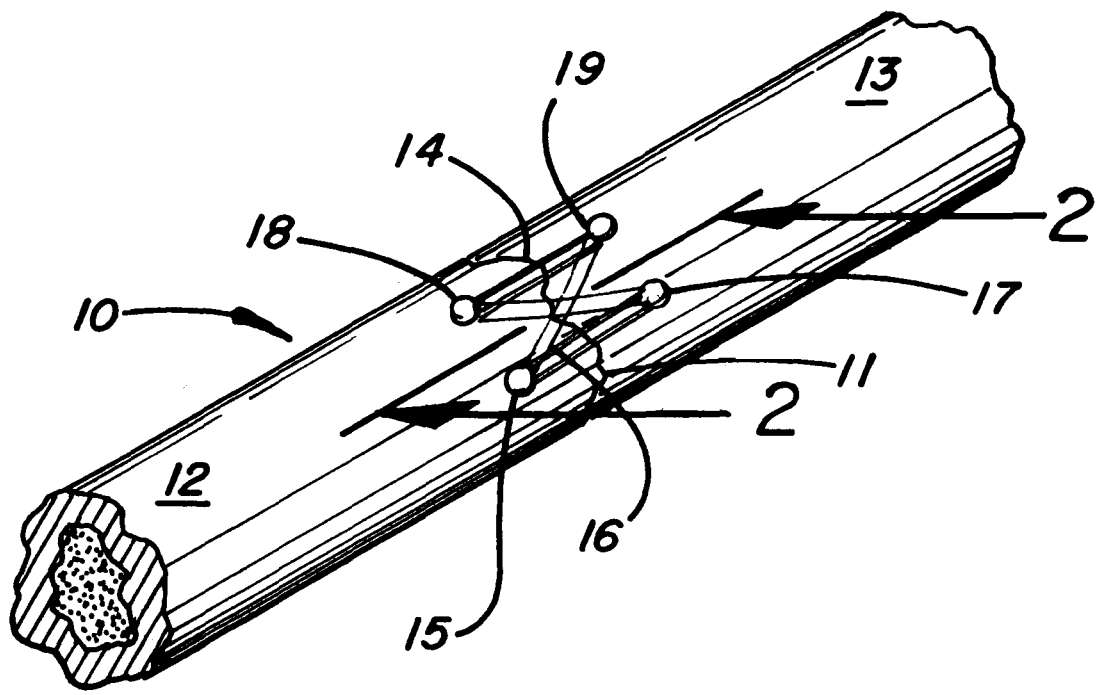
FIG. 1 is an elevational view of one apparatus and method of the present invention used to secure at least two portions of a cracked or broken bone structure to advance the healing process.

Referring now to FIG. 1 of the drawing, a bone 10 is shown having a fracture line 11 completely fracturing bone 10 into 2 separate pieces 12, 13. A first arrangement 14 of pins and flexible line is provided on one side of bone 10 spanning fracture line 11. Thus, a first pin 15 is set into bone piece 12 located at a predetermined distance, such as 8 mm, from fracture line 11. A line 16 of flexible material is secured to pin 15 in any suitable manner and led to a second pin 17, set into bone piece 13, spaced a predetermined distance, such as 8 mm, from fracture line 11 on the other side thereof. Line 16 wraps around pin 17 and any slack in line 16 is taken out then a set amount of stretch (tension) is applied. The line 16 is now extended to and wrapped around a third pin 18, set into bone piece 12, also spaced a predetermined distance from fracture line 11, such as 8 mm. Pin 18 may be about 10 mm or so from pin 20. Line 16 is again tensioned between pins 17 and 18 and then extended to a fourth pin 19, set into bone piece 13 a predetermined distance from fracture line 11, and also about 10 mm from pin 17, and 8 mm from line 11, and is wrapped around pin 19 and tensioned. Line 16 is then extended back to first pin 15, put under tension, and wrapped around pin 15. Separate lines or bands 16 may be used, if desired.

Line 16 can be now secured to pin 15 or extended, again under tension, back around pin 17, over to pin 18 and back to pin 19 and secured thereto as shown in FIG. 1.

Figure 2:
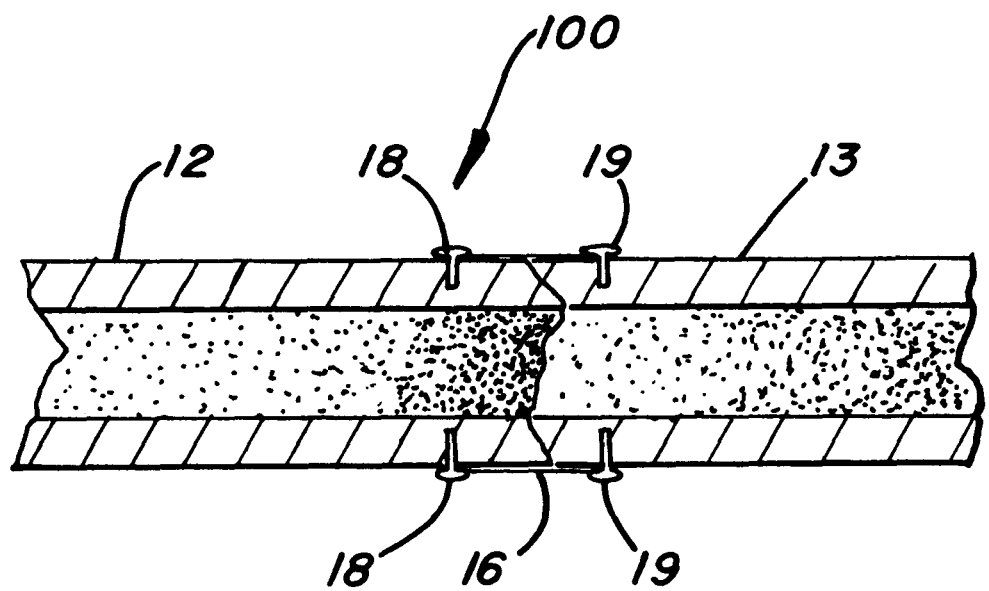
FIG. 2 is a cross-sectional view through FIG. 1.

As seen in FIG. 2, an identical arrangement 100 of pins and flexible line is made on the side of bone 10 diametrically opposite arrangement 14 and further illustration is deemed unnecessary.

Figure 3:
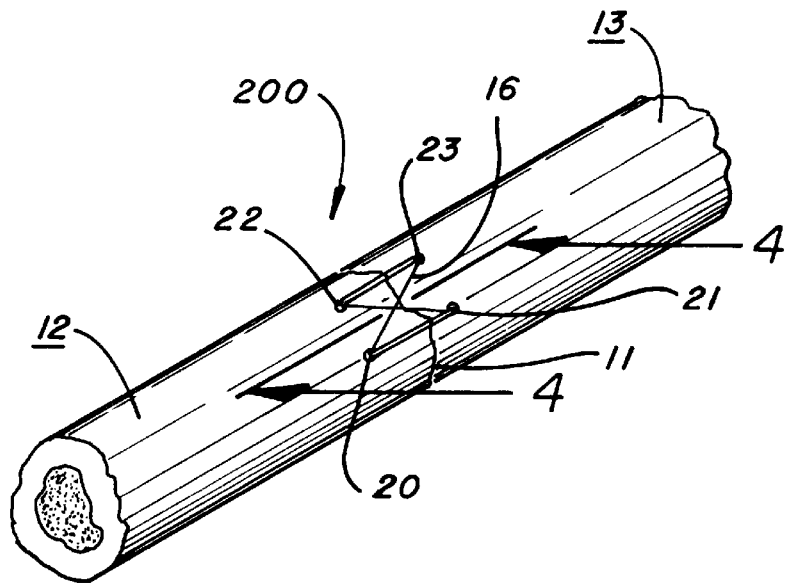
FIG. 3 is a view similar to FIG. 1 showing an alternate method and apparatus.
Figure 4:
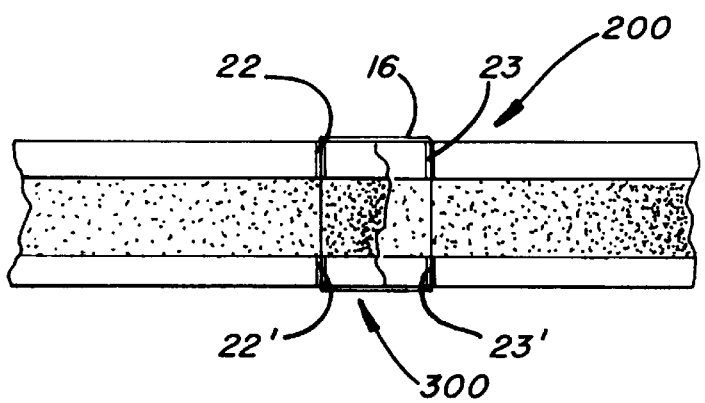
FIG. 4 is a cross-sectional view through FIG. 3.
Figure 5:
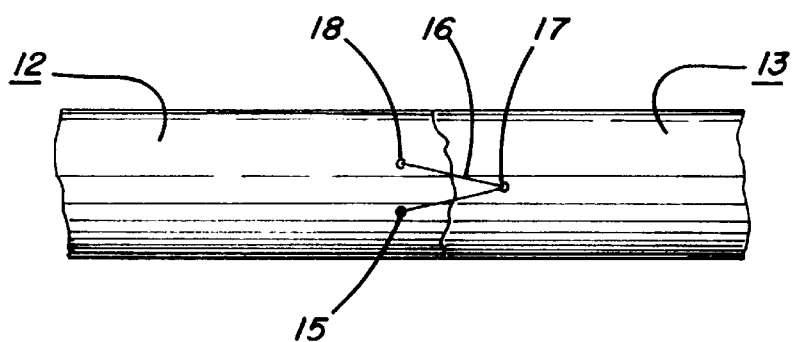
FIG. 5 is a view similar to FIG. 1 of another embodiment of the invention.

Although pins have been disclosed which may be forced into bone 10 in any suitable manner, other means, such as screws, may be used with line 16 wrapped therearound under the head of the pin or screw as appropriate. Also, as seen in FIG. 3, wherein like numerals refer to like parts of the arrangement of FIG. 1, instead of pins or screws or the like, an arrangement 200 having a plurality of spaced holes, such as holes 20 to 23 (corresponding to pins 15, 17, 18, 19, respectively, and their spacing from line 11), may be drilled or otherwise formed into bone pieces 12, 13. Similar holes 20', 21', 22', and 23', are formed opposite holes 20 to 23 (see FIG. 4 —holes corresponding to 20, 21 on the opposite side from the view shown in FIG. 3 are not visible in FIG. 4). Line 16 thus starts at hole 22 (secured therein in any suitable manner, such as an enlarged knot), then extends to and down to hole 22' on the opposite side of bone 10 (FIG. 4) using a needle or the like, across to and through hole 23' and out of hole 23 across back to and down hole 20 etc. similarly to FIG. 1. As seen in FIG. 5, where again like numerals refer to like parts of the invention, only 3 pins 15, 17, and 18 are used with line 16 extending therebetween as previously discussed.

It can be appreciated that the best method for the promotion of bone healing is to place the bone fracture fragments in accurate and rigid reduction. The concern is not just for the expeditious repair of the bone fracture but for the deleterious effects on muscle, tendons, ligaments, and joints as well.

Briefly, there are four stages to the fracture healing process. The first is the break or energy failure itself and the reuniting of the bone fragments. The second stage is called the inflammation period. The time period is within zero to five days depending upon the chance of infection, instability, and trauma. The third stage is the repair stage comprising approximately the fourth to fortieth days. This is the time of soft and hard callus formation. Callus is new tissue that forms at and around the fracture site to join the fragments for healing. It stabilizes the break area so bone growth can commence. The final stage is the remodeling stage, beginning at three to four weeks and continuing until the fragments are firmly united with new bone. The fracture site is now clinically and roentgenographically healed. The average elapsed time in an adult is three to four months for major long bones using conventional treatment means.

There are three requirements for the haversian remodeling (of bone) across the fracture site: a) exact reduction (axial alignment), b) stable fixation, and c) sufficient blood supply. Also a critical phase of fracture healing involves the formation of an intact bony bridge between the fragments. Because this involves the joining of hard tissue, it follows that the whole system must become immobile at least momentarily. At this stage of healing, inefficient fracture immobilization may lead to hypertropic non-union. This occurs because of the persistence of fibrous tissue or fibrous transformation of osteogenic callus tissue between the frontiers of bridging external callus. There is a narrow window for permissible interfragmentary motion, and the use of fixation flexibility as a method of callus stimulation at this stage would be difficult when the fracture-healing pathway has already committed to certain biological and mechanical conditions. Lastly, rigid immobilization of the fracture can shortcut this healing process. If rigid immobilization of a fracture is not achieved, fracture repair is mainly a primary callus and external bridging response. See Heppenstall, R. Bruce, "*Fracture Treatment and Healing*," W. B. Sanders Co., Philadelphia 1980. With rigid immobilization that form is suppressed and the fracture heals by medullary callus and primary cortical healing.

There is plentiful evidence that immobilized bone and bone in compression shortens the normal physiology of healing. It appears that the ideal healing environment is created by holding the bone fragments in tight approximation while allowing a tiny amount of load variability, which encourages bone regeneration.

A primary signal for bone growth is electric potential. In normal activity, bone under external stress is continuously remodeling itself, always laying down new bone to deal with forces by compression. It uses a piezoelectric effect to generate an electric potential for this signal. See Brighton, Carl T., "*Biophysics of Fracture Healing*" and "*Fracture Treatment & Healing*" edited by R. Bruce Heppenstall 1980.

Martin, R. B., "*Theoretical analysis of the piezoelectric effect in bone*" Journal of Biomechanics 12 55–63 1979, and Yasuda, I., "*Piezoelectricity of Living Bone*" J. Kyoto Pref. Univ. Med. (1953) 53:325. An electropositive potential on the tension side of stressed bone and an electronegative potential on the compressed side. The electropositive signal triggers bone resorption (tension side), the electronegative signal triggers bone growth (compression). This stress generated electric potential arises when the bone is put into compression and is not dependent on cell viability. Research has also shown that the electrical signal comes from the organic component of bone and not from the mineral component. "That is to say even if the bone is completely decalcified, these stress-generated signals are obtained."

The invention herein puts into practice this bone physiology to promote early bone healing and to keep the joints mobile thus reducing therapy time as well. A bone fracture is reduced and held in compression by elastic tension bands. The band may be made of any suitable tough elastomer capable of placing a predetermined compressive load across the fracture site.

Although a spacing of 8 mm has been suggested, the first two pins may be approximately 7–10 mm from the proximal end of the fracture on one side and 7–10 mm from the end of the distal fragment on the other side. The fracture is reduced and an elastic band is fixed between the first two pins with a set amount of tension. Although a single elastic band on line 16 has been disclosed, separate lines or bands may be used. Thus, a set of holes 22, 23 with an additional band (on the same back) is placed parallel to the first two holes 20, 21 at about 10 mm apart. This pair of tension bands or single band is now duplicated diametrically opposite the first pair of holes 20, 21 to complete the fixation. These dimensions of distances and holes/elastomer sizes will vary with bone size.

There can be many modifications of this basic arrangement; besides setting the tension bands parallel to the axis of the bone as just described they can also be placed in a cross diagonal arrangement for increased resistance to torque on the fracture.

The objective is to reduce the bone fracture with sufficiently high compression as to hold it in place (complete stability), using the compression at the fracture to promote early bone healing and to provide sufficient fixation to allow early mobility of the limb.

This concept may be applied to comminuted fractures and may also be used in conjunction with a bone plate, intramedullary rod or other fixation system where the tension in the bands is adjusted up or down to maintain position of the bone fragments.

Any suitable instruments can be used, such as manually operated devices that operate like a staple gun with manual take-up and set of the elastomer to a more complex powered micro-screwdriver (or impulse driver) with an automatic sequencer for take-up and set of the bands on line 16.

The tensioned bands 16 and pins combination provides a stable, reduced fracture in tight compression in order to promote quick healing and to provide sufficient structural integrity to allow movement of the limb.

In a study reported in "Improved Fracture Healing With Less Rigid Plates," by A. Foux, et al., Clinical Orthopaedics and Related Research, No. 339, pp. 232–245, dated June 1997, the authors reported, at page 239, that their tests showed that placing bone fragments in compression resulted in much faster recovery times than conventional bone repair procedures. The techniques of this invention, when used to repair bone fragments, results in fast recovery times.

Although particular embodiments of the invention are disclosed, variations thereof may occur to an artisan and the scope of the invention should only be limited by the scope of the appended claims.

I claim:

1. Apparatus for fixing a pair of broken bone pieces, broken along a fracture line of a bone comprising:

a resilient means;

a first anchoring means placed on one of said bone pieces;

a second anchoring means placed on the other of said bone pieces;

said resilient means interconnecting said first and said second anchoring means, such that a continuous active compressive force is applied across the entire fracture line to keep said broken bone pieces in alignment and in physical contact with each other and an additional anchoring means, and a second resilient means secured to said additional anchoring means located on the diametrical opposite side of said broken bone pieces mirroring said first and second anchoring means and said resilient means.

2. The apparatus of claim 1 wherein said first and said second anchoring means being aligned with each other and said resilient means applying continuous active compression force along a direction transverse the fracture line.

3. The apparatus in claim 1 wherein said anchoring means is a pin.

4. The apparatus in claim 1 wherein said anchoring means is an opening.

5. The apparatus in claim 4 wherein said opening adapted to extend thru said bone pieces and said resilient means passes through said openings.

6. The apparatus in claim 1 wherein said resilient means is an elastomeric strand.

7. The apparatus in claim 6 wherein said elastomeric strand includes double strands.

8. Apparatus for fixing a pair of broken bone pieces, broken along a fracture line of a bone comprising:

a resilient means;

a first anchoring means adapted to be secured on one of said bone pieces;

a second anchoring means adapted to be secured on the other of said bone pieces;

and said resilient means interconnecting said first and said second anchoring means, such that a continuous active compressive force is applied across the entire fracture line to keep said broken bone pieces in alignment and in physical contact with each other;

a third anchoring means placed adjacent to and on the same side with said first anchoring means;

a fourth anchoring means placed adjacent to and on the same side with said second anchoring means, and said resilient means further interconnecting said second anchoring means to said third anchoring means, and said first anchoring means to said fourth anchoring means and said third anchoring means to said fourth anchoring means; and an additional anchoring means and a second resilient means coupled to said additional anchoring means adapted to be secured on the diametrical opposite side of said broken bone pieces mirroring said first, second, third, fourth anchoring means and said resilient means.

9. Apparatus for fixing broken bone pieces broken along a fracture line of bone comprising:

a first elastomeric resilient strand anchoring means adapted to be secured in one of said bone pieces adjacent said fracture line, a second elastomeric resilient strand anchoring means adapted to be secured in the other of said bone pieces adjacent said fracture line opposite said first anchoring means and aligned therewith, a third elastomeric resilient strand anchoring means adapted to be secured in one of said bone pieces spaced from said first anchoring means adjacent said fracture line, a fourth elastomeric resilient strand anchoring means adapted to be secured in the other of said bone pieces adjacent said fracture line opposite said third anchoring means and aligned therewith, and resilient strand means resiliently interconnecting all of said anchoring means placing a continuous active compressive force transversely across the entire fracture line at all locations therealong, said first and second anchoring means being resiliently interconnected by at least one strand of said resilient means and said second and third anchoring means being resiliently interconnected by at least one strand of said resilient means, said second and third anchoring means being resiliently interconnected by at least one strand of said resilient means and said third and first and fourth anchoring means being resiliently interconnected by at least one strand of said resilient means, said strands between said first and fourth anchoring means and between said second and third anchoring means crossing to form an X; and a second bone repair arrangement identical to the first bone repair arrangement formed on the diametrical opposite side of said first bone repair arrangement.

10. Apparatus for fixing a pair of broken bone pieces broken along a fracture line of a bone comprising:

a first bone repair arrangement including a first pin adapted to be secured to one of said bone pieces adjacent said fracture line, a second pin adapted to be secured to the other of said bone pieces adjacent said fracture line opposite said first pin and aligned therewith, a third pin adapted to be secured to one of said bone pieces spaced from said first pin adjacent said fracture line, a fourth pin adapted to be secured to the other of said bone pieces adjacent said fracture line opposite said third pin and aligned therewith, and elastomeric resilient strand means resiliently interconnecting all of said pins placing a continuous active compressive force transversely across the entire fracture line at all locations therealong, said first and second pins being resiliently interconnected by at least one strand of said resilient means and second and third pins being resiliently interconnected by at least on strand of said resilient means and said third and first and fourth pins being resiliently interconnected by at least one strand of said resilient means, said strands between said first and fourth pins and between said second and third pins crossing to form an X; and a second bone repair arrangement identical to the first bone repair arrangement formed on the diametrical opposite side of said first bone repair arrangement.

11. Apparatus for fixing broken bone pieces broken along a fracture line of bone comprising:

a first bone repair arrangement having a first hole adapted to be placed in one of said bone pieces adjacent said fracture line, second hole adapted to be placed the other of said bone pieces adjacent said fracture line opposite said first hole and aligned therewith, a third hole adapted to be placed in one of said bone pieces spaced from said first hole adjacent said fracture line, a fourth hole adapted to be placed to the other of said bone pieces adjacent said fracture line opposite said third hole and aligned therewith, and elastomeric resilient strand means resiliently interconnecting all of said holes placing a continuous active transversely across said entire fracture line at all locations therealong, compressive force, said first and second holes being resiliently interconnected by at least one strand of said resilient means and said second and third holes being resiliently interconnected by at least one strand of said resilient means, said second and third holes being resiliently interconnected by at least one strand of said resilient means and said third and first and fourth holes being resiliently interconnected by at least one strand of said resilient means, said strands between said first and fourth holes and between said second and third holes crossing to form an X; and a second bone repair arrangement identical to the first bone repair arrangement formed on the diametrical opposite side of said first bone repair arrangement.

* * * * *